（12) United States Patent
Kraft et al.

(10) Patent No.: US 6,891,177 B1
(45) Date of Patent: May 10, 2005

(54) ION BEAM SCANNER SYSTEM AND OPERATING METHOD

(75) Inventors: Gerhard Kraft, Darmstadt (DE); Ulrich Weber, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/890,897

(22) PCT Filed: Feb. 11, 2000

(86) PCT No.: PCT/EP00/01149

§ 371 (c)(1),
(2), (4) Date: Nov. 2, 2001

(87) PCT Pub. No.: WO00/49624

PCT Pub. Date: Aug. 24, 2000

(30) Foreign Application Priority Data

Feb. 19, 1999 (DE) ......................... 199 07 098

(51) Int. Cl.[7] ............................. G21K 1/00; G21K 1/02; G21K 1/04; H01J 29/46; H01J 5/18
(52) U.S. Cl. ............................. 250/505.1; 250/292.1; 250/492.3; 378/149; 378/152; 378/203
(58) Field of Search ................................. 250/374, 389, 250/492.1, 492.21, 492.3, 505.1; 378/65, 68, 152, 203, 149; 363/16

(56) References Cited

U.S. PATENT DOCUMENTS

| | | | | | |
|---|---|---|---|---|---|
| 4,510,613 | A | * | 4/1985 | Caugant et al. | 378/152 |
| 4,596,932 | A | * | 6/1986 | Buffa et al. | 250/374 |
| 4,726,046 | A | * | 2/1988 | Nunan | 378/65 |
| 4,868,843 | A | * | 9/1989 | Nunan | 378/152 |
| 5,039,867 | A | * | 8/1991 | Nishihara et al. | 250/492.3 |
| 5,442,675 | A | * | 8/1995 | Swerdloff et al. | 378/65 |
| 5,585,642 | A | | 12/1996 | Britton et al. | 250/492.3 |
| 5,894,503 | A | * | 4/1999 | Shepherd et al. | 378/203 |
| 6,034,377 | A | * | 3/2000 | Pu | 250/492.3 |
| 6,127,688 | A | * | 10/2000 | Wu | 250/505.1 |
| 6,225,633 | B1 | * | 5/2001 | Sun et al. | 250/389 |
| 6,256,591 | B1 | * | 7/2001 | Yoda et al. | 702/57 |
| 6,275,564 | B1 | * | 8/2001 | Ein-Gal | 375/68 |
| 6,466,455 | B2 | * | 10/2002 | Kirbie | 363/16 |
| 6,529,387 | B2 | * | 3/2003 | Kirbie | 363/16 |

FOREIGN PATENT DOCUMENTS

| | | | | | |
|---|---|---|---|---|---|
| EP | | 223432 A | * | 5/1987 | ............ A61B/6/00 |
| EP | | 417965 A | * | 3/1991 | ............ A61B/6/04 |
| EP | | 0 779 081 AS | | 6/1997 | |
| EP | | 779081 A2 | * | 6/1997 | ............ A61N/5/10 |
| EP | | 826394 A2 | * | 3/1998 | ............ A61N/5/10 |
| WO | WO 9619262 A1 | | * | 6/1996 | ............ A61N/5/10 |

\* cited by examiner

*Primary Examiner*—Nikita Wells
*Assistant Examiner*—Mary El-Shammaa
(74) *Attorney, Agent, or Firm*—Frommer Lawrence & Haug LLP; Ronald R. Santucci (57) ABSTRACT

The invention relates to an ion beam scanning system having an ion source device, an ion acceleration system and an ion beam guidance system comprising an ion beam outlet window for a converging centered ion beam, and a mechanical alignment system for the target volume to be scanned. For that purpose, the ion acceleration system can be set to an acceleration of the ions required to obtain a maximum depth of penetration. The scanning system also has energy absorption means arranged in the path of the ion beam between the target volume and the ion beam outlet window transverse to the center of the ion beam. The energy absorption means can be displaced transverse to the center of the ion beam in order to vary the energy of the ion beam, so enabling, in the target volume, depth modulation of the ion beam, which is effected by means of a linear motor and the transverse displacement of the energy absorption means, with depth-staggered scanning of volume elements of the target volume in rapid succession. The invention relates also to a method of ion beam scanning and a method of operating an ion beam scanning system using a gantry system.

30 Claims, 9 Drawing Sheets

ION BEAM SCANNER SYSTEM AND OPERATING METHOD

The invention relates to an ion beam scanning system and to a method of operating the system according to the preamble of claims 1 and 20.

Such a system is known from Specification U.S. Pat. No. 5,585,642 and is used in particle therapy. The ion beam therapy that can be carried out on tumour tissue using such a system is distinguished primarily by a better dose distribution, that is to say a higher tumour dose, and the fact that it reduces the radiation to which healthy tissue is subjected, compared with X-ray therapy. That dose distribution is the result of the physical properties of particle beams, which have an inverse dose profile, that is to say the dose increases with the depth of penetration. As a result, the tumour dose can be increased compared with the conventionally possible dose obtained by customary radiation therapy.

In order to obtain as good an adaptation as possible of the irradiated volume to the predetermined target volume, in current clinical practice there are used devices for passive beam formation, which are not, however, able to solve the problem satisfactorily. Such beam formation devices work with a divergent ion beam that irradiates a larger area than the target volume, that is to say than the volume of the tumour, but restrict the divergent ion beam to the tumour volume by appropriate edge-delimitation devices and by the compensation shapes made of compensation materials, which are modelled on the outline of the tumour. Such systems and methods have the disadvantage that a high ion beam energy is required for the divergent ion beam and it is not possible to target specifically individual volume elements of a target volume or tumour.

In order to be able to target individual volume elements specifically and to be able to adapt a radiation dose optimally for the volume element, a raster scanning device for ion beams was developed. By means of that device, the target volume is broken down into layers of identical particle range and a fine, intensity-controlled pencil beam of ions is guided over the individual layers in the form of a raster. Together with the active energy variation by means of an ion accelerator, it is thus possible to achieve precise illumination in three dimensions of any desired target volume.

That intensity-controlled raster scanning device, however, also has considerable disadvantages. Firstly, a complicated control system for monitoring the beam localisation in the microsecond range is necessary. There is also the risk of fragmentation of isoenergy steps as a result of non-homogeneities of density. It is also problematic to maintain the predetermined lateral beam position (focal point of the beam), especially in the event of variation in the energy and beam width during treatment. Finally, the edge cut-offs of the target volume, which are dependent on the width of the beam profile, are disadvantageous for precise irradiation of the target volume.

Those problems mean that the adjustment and control of the beam parameters of such a device take much more time than does the actual patient irradiation. Moreover, the combination of raster scanning device for ion beams and a movable rotatable ion beam guidance system of U.S. Pat. No. 5,585,642, a gantry system, as is proposed in expert circles, represents a considerable technical challenge.

In the case of incorporation of the raster scan in a gantry system, as is known from Specification EP 0 779 081 A2, the control procedures are even more time-consuming and complicated than in rigid beam guidance achieved hitherto.

Moreover, magnets having large apertures are required for incorporation of the proposed raster scanning device in order to achieve practicable sizes in the irradiation fields. Combined with a rapid variation in energy, the large apertures of that proposed solution and thus the required screening-off of scatter fields excludes the use of superconducting magnets. Incorporation of a scanner system thus results in large apertures, that is to say in large deflection magnets and long gantry systems that take up a lot of space and are expensive. In an arrangement of the scanner system behind the last deflection magnet, that is to say downstream of the ion beam guidance system and downstream of an outlet window for the ion beam from the guidance system, as is known from Specification EP 0 779 081 A2, small apertures are possible, that is to say compact magnets can be used, but result in gantry radii of more than 7 m because of the necessary drift length or the internal width for a treatment room. Accordingly, disadvantageously, in both cases masses of more than 100 tons have to be moved with millimeter-precision accuracy.

The problem of the invention is to overcome the disadvantages of the prior art and especially, compared with the proposed ion beam raster scanning device, to provide an ion beam scanning system that overcomes the current difficulties.

That problem is solved by the subject matter of claims 1 and 20. Further features of preferred embodiments of the invention are given in the dependent claims.

In order to solve the problem, there is provided an ion beam scanning system having an ion source device, an ion acceleration system and an ion beam guidance system comprising an ion beam outlet window for a converging centred ion beam, to which there is connected a mechanical alignment system for the target volume to be scanned. Such alignment systems are known from the prior art and are intended to ensure that the target volume can be irradiated from any determinable angle in the room. Accordingly, such an alignment system customarily comprises a patient-carrying table that can be rotated about at least one axis of rotation and that can be moved in three displacement directions which, after alignment, customarily (in some cases) are not further altered during irradiation.

In the ion beam scanning system according to the invention, the ion acceleration system can be set to an acceleration of the ions required to obtain a maximum depth of penetration, and the scanning system comprises energy absorption means that are arranged in the path of the ion beam between the target volume and the ion beam outlet window transverse to the centre of the ion beam and can be displaced transverse to the centre of the ion beam in order to vary the energy of the ion beam. In order to modulate the depth of the ion beam, according to the invention for that purpose the energy absorption means are displaced transverse to the ion beam by means of a linear motor, it advantageously being possible to carry out, in the target volume, depth-staggered scanning of volume elements of the target volume in rapid succession.

That ion beam scanning system, which is based on depth modulation, offers an advantageous improvement over the installation and incorporation of a raster scanning system into a gantry system. The system according to the invention enables dose distribution that is as good as that achieved with the raster scanning system, but requires a substantially less complicated control system. Moreover, it permits compact construction even in conjunction with superconducting magnets, so that with that system it is possible to achieve any desired field sizes. Finally, with that system the healthy tissue above a tumour tissue is spared to a greater extent and in particular the skin is spared better. Moreover, the ion beam scanning system according to the invention can be used universally both for rigid ion beam guidance systems and for rotatable ion beam guidance systems.

In a preferred embodiment of the ion beam scanning system, the energy absorption means have absorber wedges that can be displaced transverse to the centre of the ion beam, which absorber wedges are driven by a high-performance linear motor, so that beam-intensity-controlled depth-scanning can be carried out. The absorber wedge system modulates the depth of penetration of the beam by means of retardation, that is to say the Bragg maximum is modulated over the tumour depth. Lateral movement can be effected by displacing the patient in two directions, for example in the x- and y-direction of a plane. That has the advantage that only a fine pencil beam of fixed energy has to be controlled by the overall ion beam guidance system. The fixed position of the beam in that system can advantageously be guaranteed by a mechanically fixed aperture diaphragm and can also be checked by small locally resolving counters. The beam intensity can be measured by a simple ionisation chamber in order to add up the beam dose per volume element.

In a preferred embodiment, the scanning system comprises an electronic control system for the linear drive of the absorber wedges and an ionisation chamber for measuring the particle rate of the beam. The absorber wedges are moved closer together by a step, preferably of from 10 to 100 $\mu$m, when a predetermined particle count has been reached, which particle count is measured by the ionisation chamber and may be completely different for the depth step, so enabling depth-staggered scanning of volume elements of the target volume.

That embodiment has the advantage that large locally resolving detectors, which check the total radiation field, are not required. That means that the control system can be reduced considerably and the system as a whole is smaller.

Theoretically, the absorber wedge system can consist of a single absorber wedge which is moved step-wise transverse to the ion beam and which, on account of its increasing thickness, reduces the depth of penetration of the ion beam into the tissue or target volume. This results in scanning of the target volume in columns. An absorber wedge system that has only one absorber wedge has the disadvantage, however, that the absorption, and therefore also the depth of penetration, varies over the width of the ion beam. In a preferred embodiment of the invention, accordingly, the energy absorption means comprise at least two absorber wedges that can be displaced in opposite directions transverse to the centre of the ion beam. Those two absorber wedges have the same absorber wedge angle so that when the two absorber wedges are moved together stepwise, the ion beam must always pass through the same thickness of an absorber material. Even in this case, however, minimal energy differences arise over the cross-section of the ion beam since the ion beam itself converges and thus has a different cross-section at the absorber wedge faces as it moves from one absorber wedge to the second absorber wedge and is thus absorbed differently over the cross-section.

In order to reduce that effect, the energy absorption means preferably comprise two absorber wedge assemblies that can be displaced in opposite directions transverse to the centre of the ion beam. In such absorber wedge assemblies, the gap between two absorber wedges is distributed over a plurality of gaps in which the above-mentioned disadvantageous effect is obviated to a great extent by appropriate arrangement of the absorber wedges relative to one another and the gradient per wedge is reduced compared with a system having two wedges that can be displaced in opposite directions to each other.

In a further preferred embodiment of the invention, the ion beam scanning system comprises an edge-delimitation device having displaceable shutter elements between the target volume and the energy absorption means. Such mechanical edge-delimitation has the advantage that steeper edge cut-offs become possible without a complicated control system becoming necessary. For that purpose, the scanning system preferably comprises edge shutters that can be adjusted separately in the manner of an iris diaphragm for such edge-delimitation of the ion beam with respect to the target volume.

In order to irradiate preferably the whole target volume, the ion beam scanning system comprises a patient table that carries the target volume and can be displaced in a plane transverse to the ion beam in two directions of co-ordinates during an irradiation procedure.

By means of the depth modulation system according to the invention, the target volume is firstly broken down into columns about the individual target beams. Along the column the path of the beam is divided into individual positions or pixels, for which the beam coverage or beam dose has been pre-calculated. Using a mechanical retardation system for the energy absorption of the ions, which consists of a multiple wedge with a linear drive, the Bragg maximum of the beam is guided in an intensity-controlled manner without interruption from one pixel to the next pixel when the particle coverage of the individual pixels has been reached. That division into columns corresponds better to the actual circumstances of tumour irradiation than the division into flat surfaces of the proposed raster scanning device, since non-homogeneities in density upstream of the target volume, for example in the healthy tissue structure above a tumour, result in a displacement of a column in a positive or negative direction but do not result in an interruption within the column.

For the treatment of a tumour in a patient, in the solution according to the invention advantageously the highest energy required for the beam guidance system is set from the accelerator to the patient. That energy setting advantageously remains constant for the whole treatment since the depth variation, that is to say the energy variation, occurs only as a result of the rapidly movable absorber wedge system of the energy absorption means directly in front of the patient. The length of the individual irradiation columns depends upon the geometry of the target volume. The dose cross-section of the columns is a Gaussian profile. The spacings between the centres of the columns must be smaller than half the half-value width of the Gaussian distribution in order to produce continuous overlapping. In order to eliminate over-irradiated or under-irradiated positions, a relatively broad beam profile in the region of an order of magnitude of 10 mm in diameter is advantageous. Such beam profiles, which are large compared with those in the proposed raster scanning device, also reduce the duration of irradiation per patient in the case of large target volumes.

Since some of the radial dose distribution of the individual dose columns can be absorbed by the edge-delimitation device of a preferred embodiment of the invention, it is possible to obtain a steep edge cut-off at critical positions despite large half-value widths.

Whereas the energy absorption means in the form of a depth modulation device, or a depth modulator or depth scanner, can scan the target volume rapidly and in columns because of the drive of the absorber wedge system by means of a linear motor having an air bearing, there is sufficient time for lateral displacement of the target volume in the two directions x and y of a plane, so that a patient table, which carries the target volume and can be displaced in two lateral directions transverse to the ion beam during an irradiation procedure, has sufficient time to scan gradually column by column and overlap next to one another.

In a further preferred embodiment of the invention, the patient table can be displaced during treatment in only one direction of co-ordinates, whilst for the other lateral direction suitable deflection magnets for the ion beam are provided so that the ion beam can be deflected from its central position at the outlet window transverse to the lateral direction of the patient table. An advantage of that system is that it is dependent upon mechanical and thus slow movement in only one direction, and depth modulation and lateral modulation can be carried out relatively swiftly.

Preferably an ionisation chamber for summation of the ions that strike a volume element is arranged upstream of the energy absorption means and downstream of the ion beam outlet window. By means of that arrangement it is possible advantageously to determine the radiation dose, which is defined as the total number of ions that strike a volume element.

In a further preferred embodiment of the invention, the ion beam scanning system comprises, in addition to a patient table that can be displaced in a lateral direction, a gantry system that can be rotated about a gantry axis of rotation transverse to the lateral direction of movement of the patient table. Owing to the slow back and forth movement of the gantry system over the irradiation field, the individual columns are positioned adjacent to one another and thus advantageously the second dimension of the tumour-conforming irradiation is effected.

In the preferred ion beam scanning system having a gantry system, the ion beam is supplied to the gantry system in the gantry axis of rotation and aligned with a target volume by means of magneto-optics at adjustable angles of from 0 to 360° in a plane orthogonal to the gantry axis of rotation. The ion beam thus intersects the gantry axis of rotation at an isocentre of the gantry system. The gantry system comprises a target volume carrier that can be displaced laterally in the direction of the gantry axis of rotation, which target volume carrier is arranged upstream of the isocentre. The energy absorption means are arranged radially upstream of the gantry system. Volume element scanning in the depth direction is achieved by means of the depth modulation device according to the invention, angular volume element scanning in the lateral direction is defined by means of the gantry system and volume element scanning in the longitudinal direction is defined by means of the laterally displaceable target volume carrier, with the result that target volumes of any shape can be scanned by volume element by a combination of those three scanning means.

In that preferred embodiment of the invention, it is important that the isocentre of the gantry movement lies downstream of, that is to say behind, the irradiation volume. A slight conical shaping of the irradiation volume can be taken into account by appropriate weighting of the pixels in a dense network of radial support points, without loss of homogeneity.

The angular difference of the eccentric irradiation as a result of gantry rotation has the decisive advantage of further reducing the dose load in the inlet channel and thus reducing the dose to which the healthy tissue above the tumour tissue is subjected. Since, owing to its large mass, the gantry system can move only continuously or in small steps, the particle fluence supplied must be higher than the fluence required per column. That means that the irradiation of each individual column is carried out in the course of a short angular movement of the gantry system. The third co-ordinate of the irradiation is effected, in that preferred embodiment, by a slow stepwise displacement of the recumbent patient on the target volume carrier through the irradiation apparatus in the direction of the gantry axis of rotation. In that procedure, preferably speeds of less than 1 cm/s are observed and are sufficient for tolerable periods of irradiation of patients.

In a further preferred embodiment of the invention, the target volume carrier remains stationary during treatment and the ion beam is deflected in the gantry plane by the deflection magnets during irradiation. Thus, instead of displacing the patient couch, the ion beam is deflected by varying the magnetic field in the last deflection magnet in the gantry. This results advantageously in the following required movement sequence in three degrees of freedom: the beam deflection with the highest speed occurs by means of the energy absorption means, or depth modulator. At a medium speed (e.g. 4 mm every 1 to 2 s), the beam is guided in the gantry plane by the deflection magnets to the next column. The slowest movement is the rotation of the gantry, which is carried out, after the irradiation of a row of columns, by rotating the gantry system to the next row of columns. The advantage of that ion beam scanning system is that the patient does not have to be moved and the gantry system does not have to move back and forth during irradiation but can be rotated stepwise.

Compared with traditional systems, the variable deflection of the beam in the gantry plane requires only relatively little extra expense since the deflection magnets are necessary anyway. The change in the deflection of the beam takes places slowly (at a rate of seconds) and thus also no high demands are made on the magnet power supply or on the control system. A simple wire chamber, which must be selected to have a relatively low repetition rate, is sufficient as monitoring device for the deflection variation of the beam. The control electronics for that slow scanning technique of the present invention are much less complicated than the proposed rival rapid raster scanning technique in which the beam positions are to be measured every 100 $\mu$s in order to be able to track and control the beam.

In a preferred embodiment of the ion beam scanning system having a gantry system, the energy absorption means comprise absorber elements that can be displaced tangential to the circle of rotation of the gantry system. That embodiment is achieved in that the energy absorption means are fixed directly to the gantry system, namely downstream of the outlet window of the ion beam. In that embodiment of the ion beam absorption system having a gantry system, it is also possible for there to be arranged, instead of one absorber wedge, at least two absorber wedges that can be displaced in opposite directions tangential to the circle of rotation of the gantry system or radially staggered absorber wedge assemblies that can be displaced tangential to the circle of rotation of the gantry system.

In a further preferred embodiment of the ion beam scanning system having a gantry system, a central region of the target volume is arranged upstream of the isocentre by at least $\frac{1}{3}$ of the radius of the gantry system, so that the target volume itself does not lie in the isocentre. The advantages of that embodiment have already been described in detail above. It should be emphasised that an optimal spacing between the target volume and the isocentre can be set in order for the radiation to which healthy tissue is subjected to be kept low in the inlet channel of the irradiation.

In the preferred method of ion beam scanning using an ion source device, an ion acceleration system and an ion beam guidance system comprising an ion beam outlet window for a converging centred ion beam, and a mechanical alignment system for the target volume to be scanned, the following method steps are carried out:

setting of the ion acceleration system to an acceleration of the ions required to obtain a maximum depth of penetration;

detection of the ion beam intensity;

transverse displacement of energy absorption means of variable thickness for depth modulation of the ion beam;

summation of the radiation ions of a volume element of a target volume up to a predetermined radiation dose;

alteration of the depth of penetration of the ion beam by means of transverse displacement of the energy absorption means when the predetermined radiation dose of the volume element has been reached in order to irradiate the next upstream volume element.

An advantage of that method is that the acceleration of the ions in the ion acceleration system needs to be determined only once and can be maintained during the entire treatment phase. The depth modulation of the irradiation is carried out exclusively by energy absorption means arranged upstream of the target volume to be irradiated and downstream of the ion beam outlet window. Since, apart from the energy absorption means or depth modulator, there is no further material in the path of the beam before it reaches the tissue, the nuclear fragmentation is minimal and independent of the depth of penetration, since the total absorption caused by the depth modulator plus the depth of the tissue remains constant. A constant Bragg profile is thus achieved over the target volume depth. The use of special filters, also ripple filters, to render the Bragg profile uniform, as are used in conventional methods, is no longer necessary in the method according to the invention.

The movement of the absorber wedges for the depth modulation is controlled by the intensity of the incoming beam according to the calculated model of the dose distribution. The length of each irradiation column is divided into individual image points and the beam, that is to say the Bragg maximum of the beam, is advantageously shifted from one pixel, or image point, to the next when the required particle count has been reached. The method according to the invention thus offers the greatest possible safety for the patient and a high degree of precision in the irradiation of tumour tissues and minimal radiation of upstream healthy tissue.

In a preferred way of carrying out the method, an electronic control system for the linear drive of the absorber wedges moves the wedges closer together by a step after it has measured the particle rate of the beam by means of an ionisation chamber and after a predetermined number of particles, which may be different for each depth step, has been reached. Depth-staggered scanning of volume elements of the target volume is thus effected. Preferably the width of the step by which the absorber wedges are moved closer together is from 10 to 100 $\mu$m.

The measured intensity per volume element is from $10^6$ to $10^8$ absorbed ions during scanning of the target volume. The target volume can be scanned continuously progressively in that, during the depth modulation, either the patient table or the gantry or both are moved simultaneously in the other two directions. Whereas scanning of the target volume in the depth direction is always effected in columns as a result of the depth modulation, those columns can be shifted in a zig-zag manner in the case of continuously progressive scanning.

In a different preferred way of carrying out the method, the scanning of the target volume proceeds stepwise. That stepwise procedure is especially advantageous when the movements are effected at different speeds owing to different masses to be moved.

Accordingly, preferably scanning of the target volume can be carried out continuously in the depth direction and stepwise in the lateral and longitudinal directions, or scanning of the target volume can be carried out continuously in the depth direction and in the lateral direction and stepwise in the longitudinal direction. In a preferred way of carrying out the method, the ion beam scanning system is operated using a gantry system. For that purpose, the following method steps are carried out:

1. arrangement of the target volume upstream of the isocentre;
2. scanning of the volume element in the depth direction by means of energy absorption means arranged radially upstream of the gantry system;
3. scanning of the volume element in the lateral direction by altering the angle of rotation of the gantry system; and
4. scanning of the volume element in the longitudinal direction by raster displacement of the target volume carrier.

An advantage of that method is that the target volume carrier or the patient table has to be moved in only one direction during irradiation, whereas one of the other two directions is obtained by depth modulation by way of the energy absorption means and the other is carried out by the rotational or back and forth movement of the gantry system.

Whilst for the displacement of the absorber wedge system of the energy absorption means relatively small masses are to be moved using a linear motor, the rotational movement of a gantry system is effected correspondingly more slowly, whereas displacement of a patient table, owing to its lesser mass compared with a gantry system but greater mass compared with the energy absorption means, with its inertia lies between those two devices.

In a further preferred method, the patient can lie completely at rest on the patient table when a gantry system is used in which a target volume carrier is aligned before treatment and remains stationary during irradiation and the ion beam is deflected in the gantry plane by means of the last gantry deflection magnets in order to carry out volume element scanning in the longitudinal direction.

Further advantages, features and possible applications of the invention will now be explained in more detail with reference to embodiments.

Figure 1:
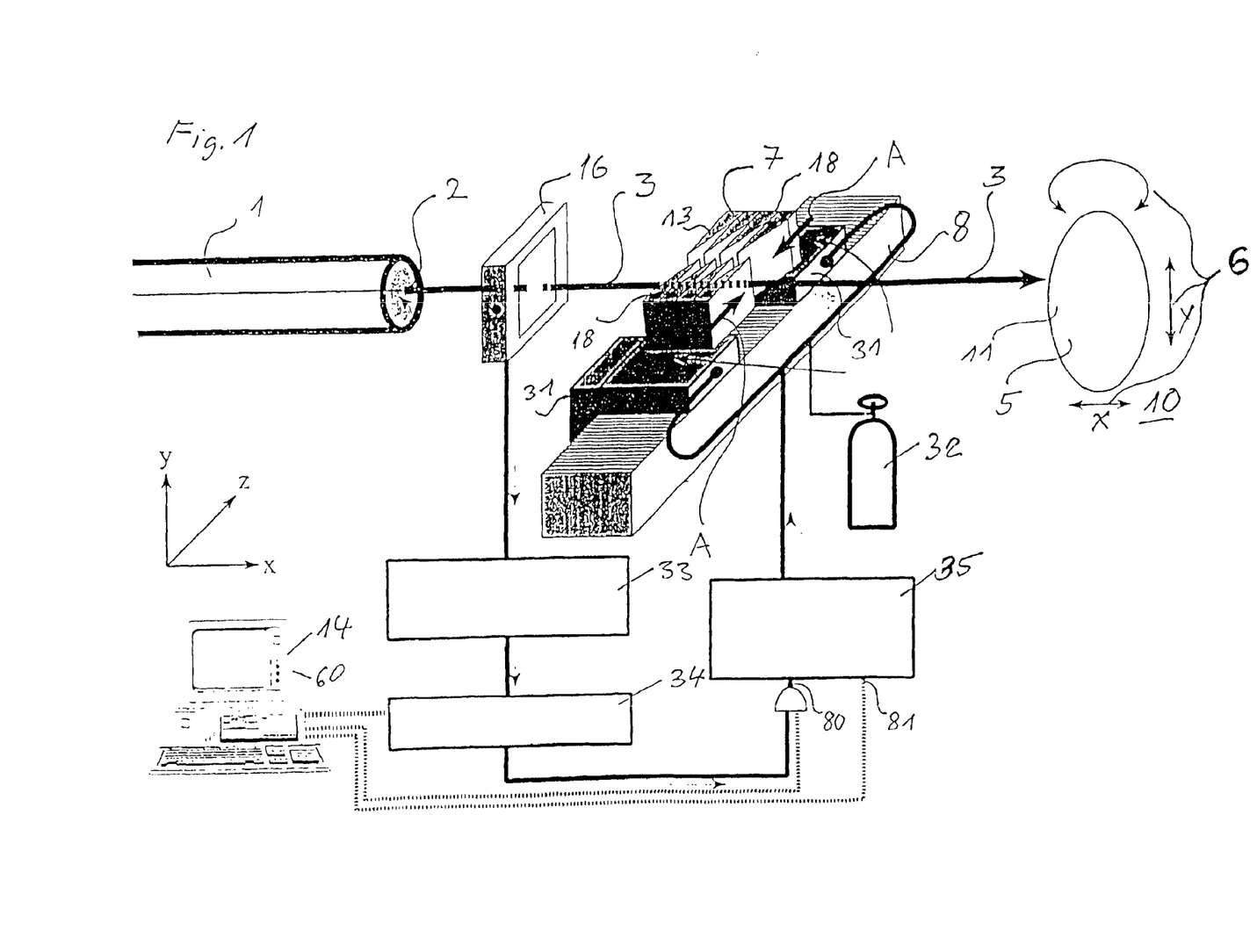
FIG. 1 is a diagrammatic representation of a first embodiment of the invention.

FIG. 1 is a diagrammatic representation of a first embodiment of an ion beam scanning system that comprises an ion source device (not shown), an ion acceleration system (not shown) and a beam guidance system 1 comprising an ion beam outlet window 2 for a converging centred ion beam 3. The ion beam scanning system includes a mechanical alignment system (not shown) for the target volume 5 to be scanned.

The alignment system enables the target volume to be rotated at least about one axis and to be displaced in the direction of three spatial coordinates so that the target volume can be irradiated by the ion beam from any desired selectable angle in the room. Such alignment is effected before the actual irradiation of the target volume with ions.

By means of the ion acceleration system (not shown), firstly an acceleration of the ions required to obtain a maximum depth of penetration is set. That energy is not altered during the entire treatment and ensures that the ion beam can penetrate the tissue to the deepest point of the target volume. By means of energy absorption means 7, which are arranged in the path of the ion beam between the target volume 5 and the ion beam outlet window 2 transverse to the centre of the ion beam and can be displaced transverse to the centre of the ion beam in the direction of arrow A in order to vary the ion beam energy, the Bragg maximum of the maximum depth of penetration is shifted to lower depths of penetration by increasing energy absorption. That procedure can be carried out continuously or stepwise so that depth modulation or depth scanning occurs, which will be referred to hereinafter also as depth scan. The change in the energy absorption is achieved by means of the energy absorption means 7 in that a linear motor 8 causes absorber wedges 13 arranged opposite one another in pairs to be displaced transversely towards one another in the direction of arrow A, so that depth-staggered scanning of volume elements of the target volume can be carried out in rapid succession.

For that purpose the rotors 31 of the linear motor 8 are mounted on air bearings and are supplied with compressed air by a compressed air cylinder 32. In order to move the absorber wedges 13 closer together stepwise, the motor currents are controlled by way of a stepper motor control 35, which has one power stage.

In order to measure and add together the number of the ions until a predetermined ion beam dose per volume element of the target volume has been reached and until the linear motor 8 can move the absorber wedges 13 closer together by a further step, preferably by from 10 to 100 $\mu$m, a pulse control having TTL pulses, the frequency of which is proportional to the ion rate occurring (ions/sec), is controlled by means of the ionisation chamber 16 by way of a current amplifier having a downstream voltage-frequency converter 33. As soon as a sufficient dose for a volume element has been reached, which corresponds to a specific TTL pulse count, the pulse control triggers the next step by a control pulse to the stepper motor control. That procedure is repeated until a depth scan has been completed.

Figure 2:
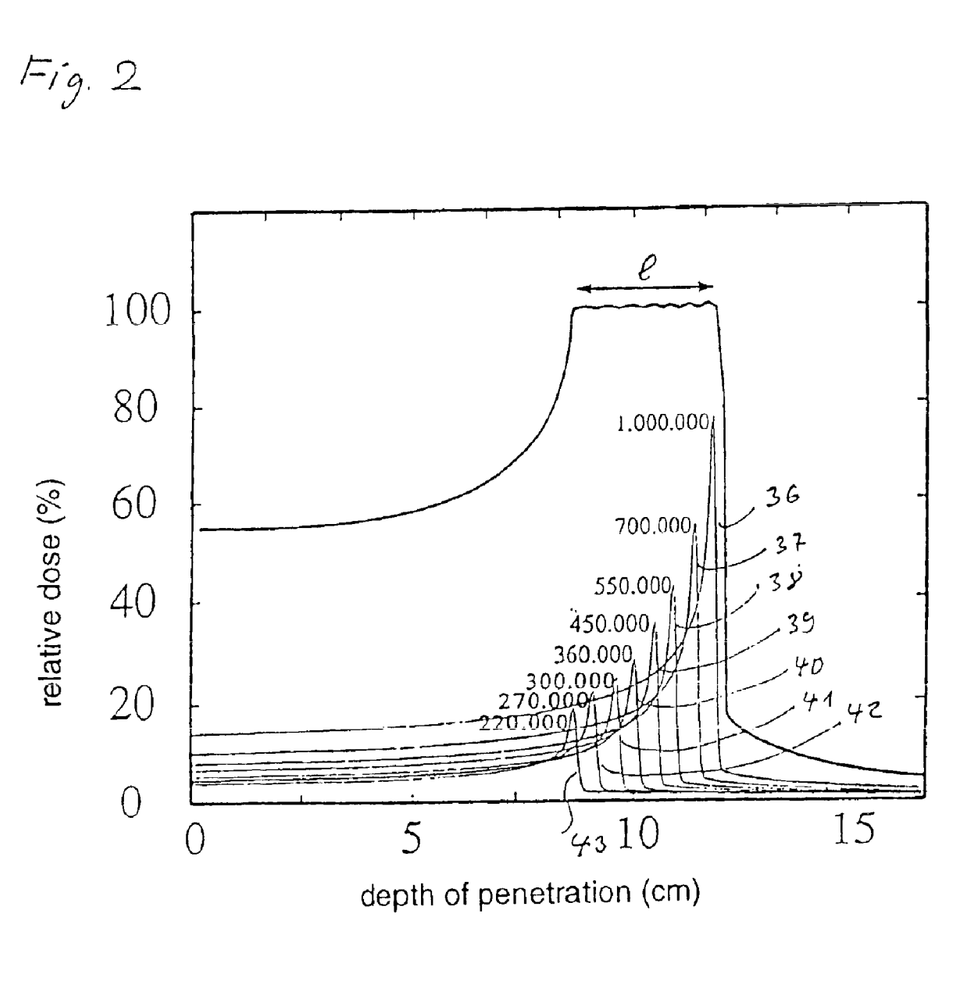
FIG. 2 shows the principle of the overlaying of depth dose profiles displaced relative to one another.

FIG. 2 shows the principle of the overlaying of depth dose profiles displaced relative to one another. By means of the depth scanner, the individual Bragg curves 36 to 44 are displaced by 4.3 mm in each case from one absorber position to the next. The height of the Bragg curves is given by the number of particles that strike the target at the corresponding absorber position. If the particle counts have been calculated correctly in advance, the overlaying of the Bragg curves yields the desired broadened Bragg peak, which corresponds to the extent of the target volume in depth. Accordingly, the depth of penetration is indicated along the abscissa in cm and the relative dose is indicated along the ordinate in %.

In that example, it can clearly be seen that when the Bragg curves are added together, the target volume is irradiated with 100% relative dose, whilst the healthy tissue above it is subjected to less than 60% of the irradiation load, and the tissue beneath it only has to absorb well below 20% of the radiation dose. The extent of the advantage of ion beam therapy over X-ray therapy thus becomes clear.

FIG. 2 is merely intended to clarify the principle of overlaying. In a real depth scan, several thousand Bragg curves having much smaller spacings are overlaid. That enables virtually continuous movement of the drives of the energy absorption means 7 and thus ensures uniform overlaying so that conventional ripple filters are no longer necessary when the ion beam scanning system according to that embodiment of the invention is used.

Figure 3:
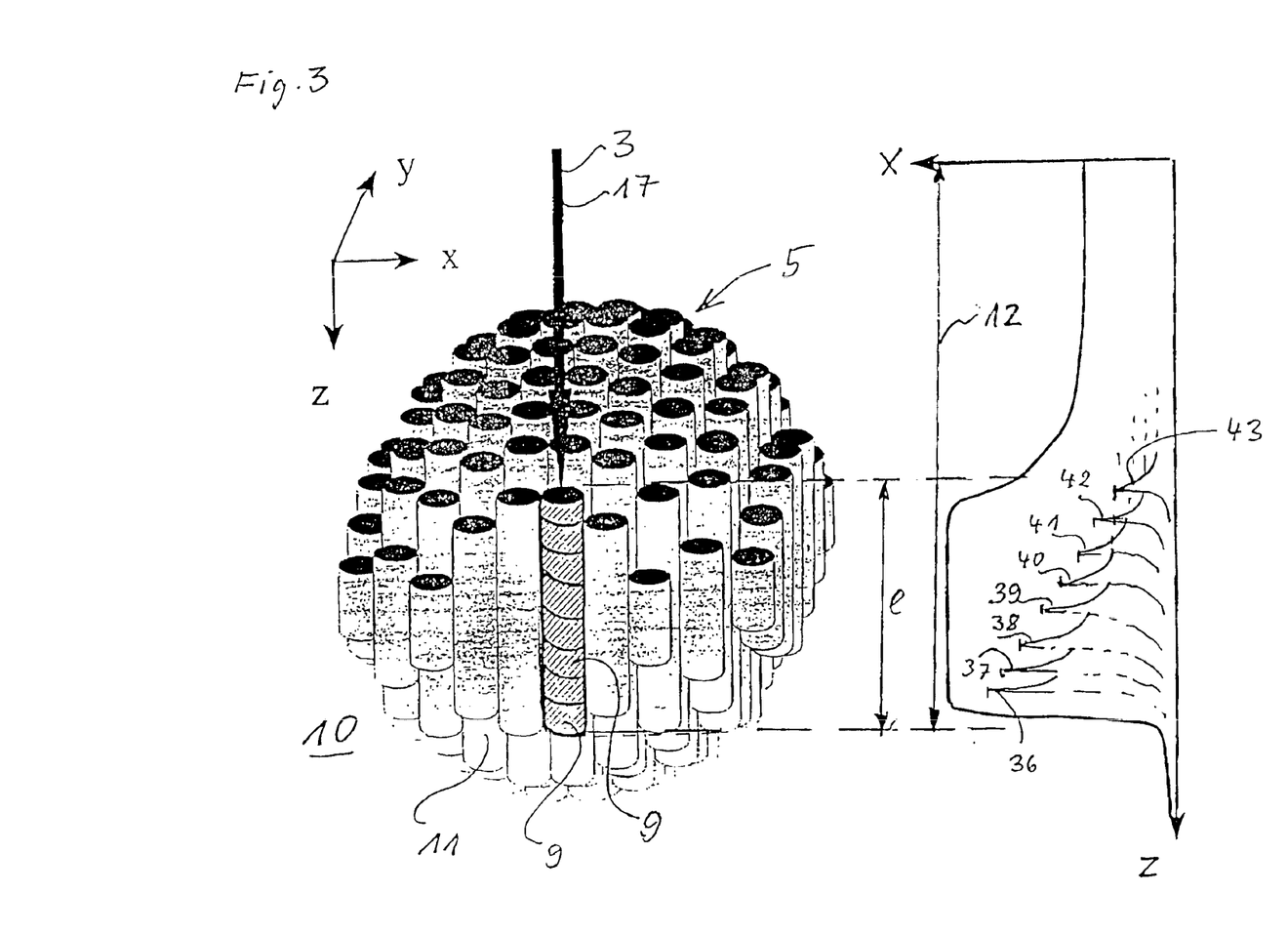
FIG. 3 shows the principle of the scanning of a target volume in columns using the embodiment according to FIG. 1.

FIG. 3 shows the principle of the scanning of a target volume in columns using the embodiment according to FIG. 1 with ion beam 3 in the ion beam direction 17 and penetrating depth of the ion beam 3 in the z-direction 12. In that embodiment, the target volume is displaced mechanically in the direction of the arrows X and Y, whilst the ion beam 3 of a rigid ion beam guidance system retains its central direction. By the depth modulation or depth scan caused by the energy absorption means, the volume elements 9 of the target volume 5 are scanned in columns, the extent 1 of the broadened Bragg peak corresponding to the length of the column or the depth of the target volume at that point by virtue of summation of the Bragg curves 36 to 43. As FIG. 3 clearly shows, healthy tissue 10 can be sparred from irradiation to as great an extent as possible, whilst the tumour tissue can assume a very wide variety of shapes, which means that only the depth modulation has to follow the extent of the tumour tissue in one direction of coordinates, for example along the z-coordinate.

Figure 4:
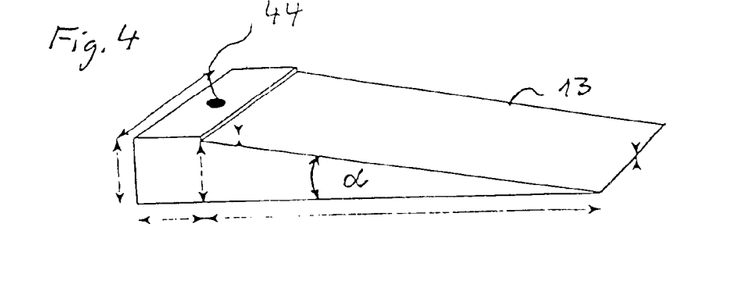
FIG. 4 is a perspective view of energy absorption means in the form of a single absorber wedge.
Figure 6:
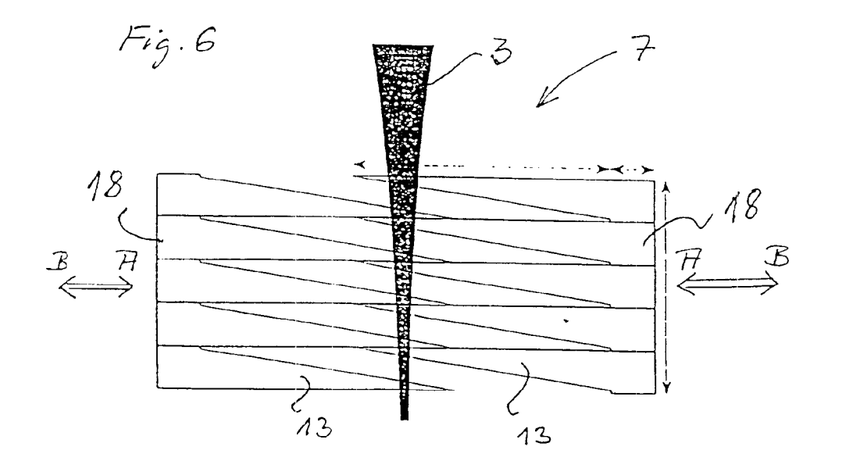
FIG. 6 is a cross-section through energy absorption means having absorber wedge assemblies each comprising five absorber wedges.

FIG. 4 is a perspective view of energy absorption means in the form of a single absorber wedge. That absorber wedge is a single wedge of an absorber wedge assembly, as shown in FIG. 6. The absorber wedge angle $\alpha$ is from 6 to 10° and in that example is set at 8.765°±0.01. The length of the absorber wedge is from 100 to 150 mm and in that example is set at 120±0.02 mm. The greatest thickness of the absorber wedge is from 15 to 30 mm and in that example is set at 19±0.01 mm. The parallelipipedal end of the absorber wedge serves for stacking it in an assembly, as shown in FIG. 6. The dimensions of the parallelipipedal end are from 15×15 $mm^2$ to 30×30 $mm^2$ with a length of from 40 to 60 mm, which, in this example, is 50 mm. The parallelipipedal cross-section is matched to the greatest absorber wedge depth of 19 mm and in this example is 20×20 $mm^2$. A central hole 44 enables a plurality of individual wedges to be combined to form absorber wedge assemblies, as shown in FIG. 6.

Figure 5:
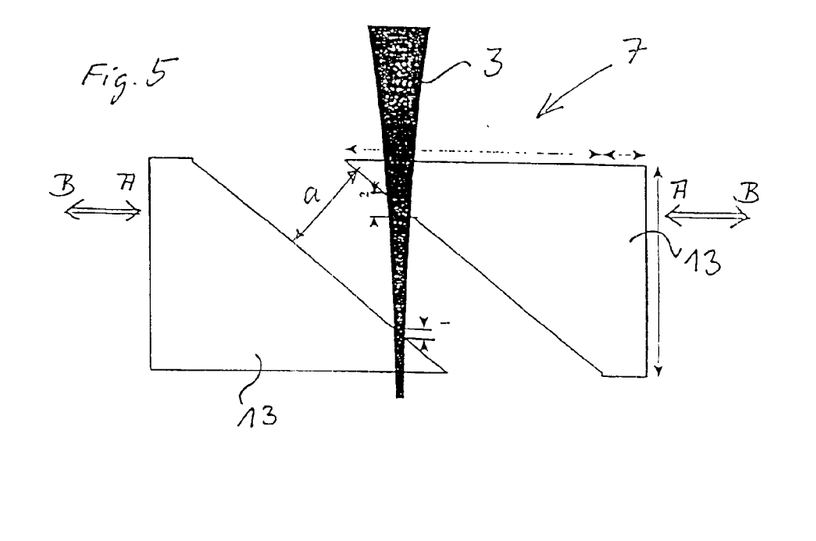
FIG. 5 is a cross-section through energy absorption means having two absorber wedges.

FIG. 5 is a cross-section through energy absorption means comprising two absorber wedges 13 that can be moved towards one another in the direction of arrow A or moved apart in the direction of arrow B. When those two absorber wedges are moved apart, the result is a greater spacing a between the inclined absorber wedge surfaces. Owing to the converging centred ion beam 3, it becomes clear that the region of the ion beam on the right-hand side of the beam has to pass through a greater thickness of absorber material than on the left-hand side of the beam. Thus the depth of penetration into the target volume viewed over the cross-section of the ion beam is different. In order to balance and minimize that, in FIG. 6 the cross-section of energy absorption means 7 comprising absorber wedge assemblies 18 each comprising five absorber wedges 13 is shown. It can clearly be seen that the right-hand side of the convergent ion beam has to penetrate scarcely more absorber material than the left-hand side. Thus, depth modulation using absorber wedge assemblies 18 is preferable to depth modulation using two absorber wedges 13, as shown in FIG. 5.

The absorber wedges 13 preferably consist of a plurality of plexiglass wedges. Placed one on top of the other as absorber wedge assemblies 18, they have the same effect as two absorber wedges 13 of FIG. 5 but with a different gradient. A large gradient is necessary in the case of two absorber wedges, as in FIG. 5, in order to obtain a sufficient absorber effect with the obtainable acceleration of the absorber wedges 13. In FIG. 6, that large gradient is distributed over a plurality of absorber wedges having a small gradient.

The advantage of having a plurality of absorber wedges 13 placed on top of one another compared with two thick absorber wedges 13 is that the beam is unavoidably scattered in the absorber wedges and, in the case of the two thick absorber wedges, some of the beam passes through more material than another part of the beam. The result is an undefined energy distribution of the beam, which it would be preferable to avoid. The absorber wedges 13 are secured to the linear motor 8 by aluminium corner pieces. The screw-fixings are precise and free of play.

Plexiglass as material for the absorber wedges 13 has the advantage that it can be processed precisely and from a radiological point of view is very similar to water. Accordingly, for a carbon ion beam a 1 cm thick plexiglass layer behaves in exactly the same manner as 1.15 cm thick water layer. When 2×4 absorber wedges having an angle of gradient of α=8.765° are used, a displacement by the motors by 1 mm increases the thickness of the absorber by a water-equivalent distance of 1.42 mm of water.

The ion beam scanning system according to the present invention makes high demands on the depth modulation system and on the mobility of the energy absorption means 7.

The energy absorption means, or depth scanner, should produce with a heavy ion beam a smooth depth dose profile having a typical dimension of from 2 to 15 cm in depth. For that purpose, there are used absorber wedges that can be so displaced that the distance through which the beam passes is altered. The depth scanner varies the absorber thickness in a precisely defined manner during beam extraction. The heavy ion beams, which have passed through absorption settings of varying thickness, are overlaid in the process and when added together produce the desired depth dose profile.

In order that, in the overlaying, there are no departures from the predetermined settings, in each setting of the absorber wedge thickness a precisely defined amount of ion beam or number of particles must strike the target. That means that when the absorber wedges remain in a certain position for too long or too short a period, there are departures from the desired depth dose profile. In order to avoid such departures, the ion beam current must be measured as a function of time and, depending on the number of ions measured, the absorber wedges are to be displaced continuously with high precision and varying step speed.

Since the ion beam current, especially in the case of heavy ions accelerated by an ion acceleration system, preferably a synchrotron, is not constant, but exhibits very large fluctuations, that non-uniform ion beam current results in the absorber wedges 13 also having to be displaced at very irregular speed and in some cases jerkily. That makes extremely high demands on the precision and dynamics of the drive and control system for such energy absorption means 7, with the result that the following parameters are preferably to be observed:

| | |
|---|---|
| Duration of extraction: | 2–4 s |
| Depth dose profile: | 2–15 cm |
| Maximum speed: | 1–2 m/s |
| Acceleration: | 20–30 m/s$^2$ |
| Precision: | 100–200 μm |

Absorber wedge assemblies as shown in FIG. 6 are used for that purpose.

In order to carry out the displacement of the absorber wedges with as great synchronicity with the measured ion beam intensity as possible, the measuring and control electronics must react relatively quickly. The reaction time, that is to say the sum of the delay time constants of the ionisation chamber 16, the current amplifier 33 and the stepper motor control 35, as shown in FIG. 1, is consequently less than 1 ms.

Figure 7:
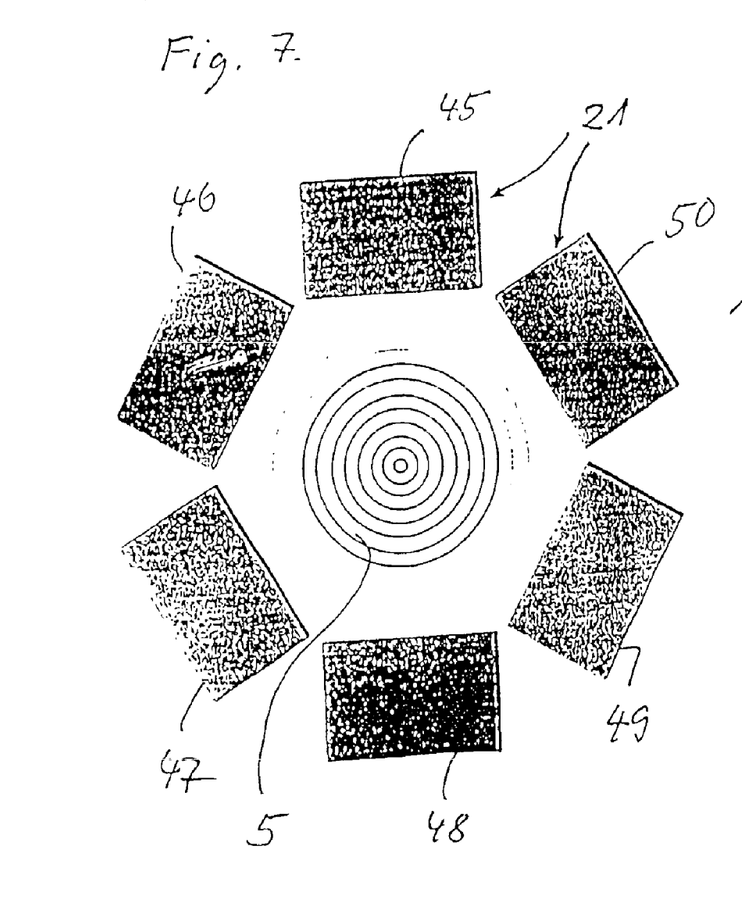
FIG. 7 shows an edge-delimitation device in the inoperative position.
Figure 8:
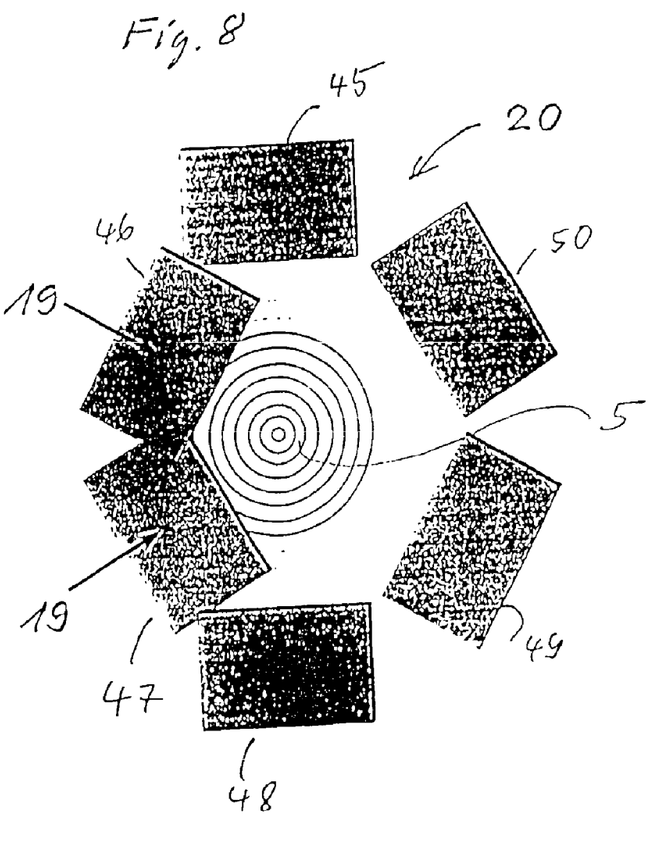
FIG. 8 shows an edge-delimitation device having two shutters in the operating position.

Lesser demands are made on the dynamics for the edge-delimination device 20. FIG. 7 shows an edge-delimination device in the inoperative position having displaceable shutter elements 21. In that example it consists of six individual rectangular tungsten plates 45 to 50, which can be displaced separately from their inoperative position shown in FIG. 7 towards the center. For that purpose, the tungsten plates 45 to 50 are arranged offset in their height, so that they do not hinder one another when they are being pushed together. When the ion beam approaches the edge of a tumour tissue, or target volume 5, the corresponding edge shutter 19, as shown in FIG. 8, can be displaced so enabling sharp delimination of the edge for the relatively broad ion beam. In principle, any edge of the tissue can be delimited even by three height-staggered shutters consisting of rectangular tungsten plates, but six plates have the advantage of offering greater variation.

Figure 9:
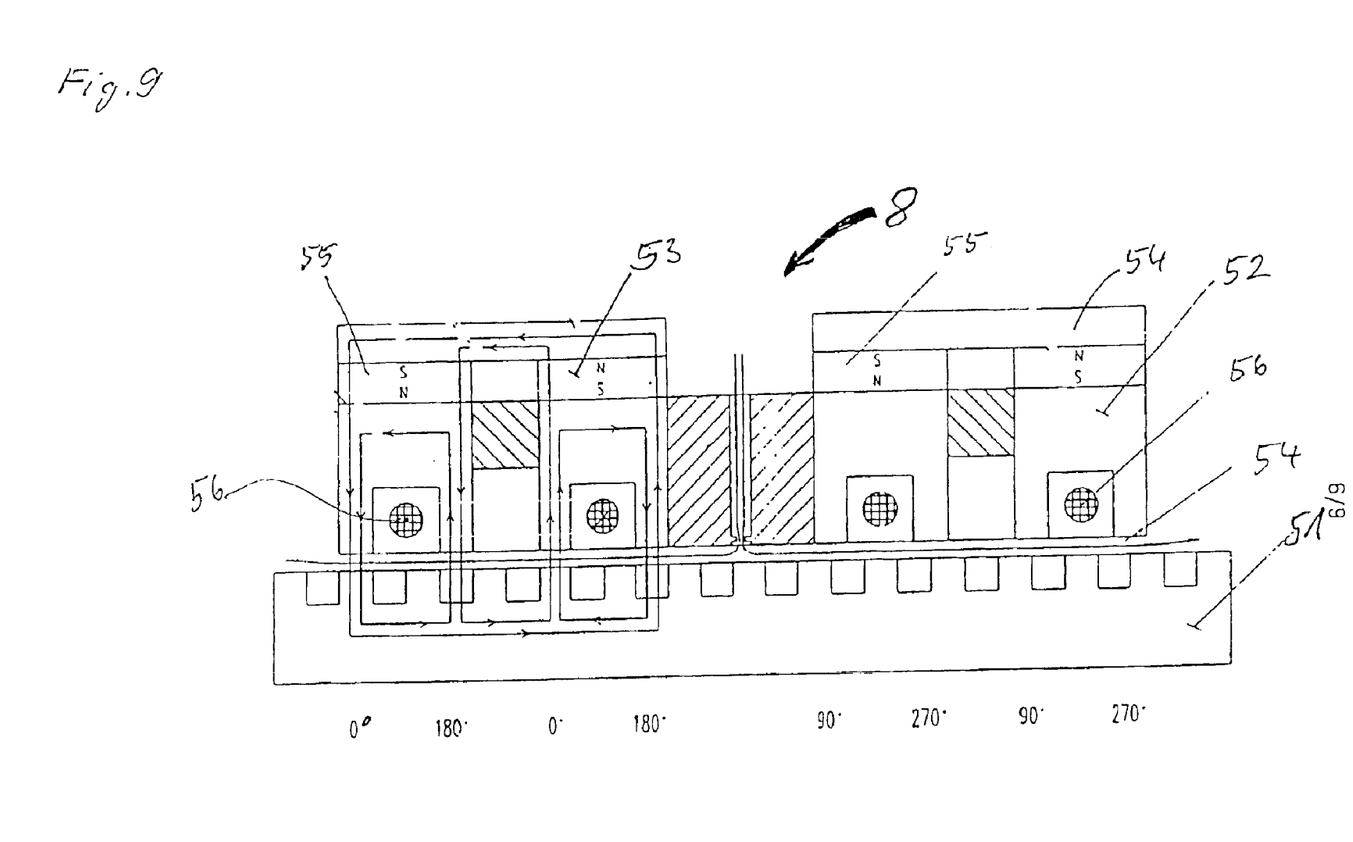
FIG. 9 is a schematic diagram of a linear motor having an air bearing.

FIG. 9 is a schematic diagram of a linear motor 8 having an air bearing, to which motor an absorber assembly 18 of energy absorption means 7 can be secured. Such a linear motor is a permanently excited two-phase reluctance motor and consists of two structural units, the stationary stator 51 and a mobile part, the rotor 52, having an air bearing.

A rotor comprises at least two magnet systems 53 and 54, each having a permanent magnet 55 as constant flux source. By means of a flow of current in the windings 56, it is possible to control the magnetic flux in the limbs, which means that in one limb a flux is amplified and in the associated other limb the flux is weakened. A dynamic effect in the direction of movement is the result of a change in the energy of the magnetic field in the air gap between the stator 51 and the rotor 52. If both windings of the magnet systems 53 and 54 are operated with laterally displaced sinoidal currents, synchronized behaviour, or a defined position for each current relationship, is obtained. The rotor element is arranged in the X-direction so that linear movements can be effected. The stator element 51 consists of structured soft iron strips which are attached by adhesion to steel bodies, cast mineral material, natural hard rock or light glass fibres or hollow carbon fibre bodies.

In order to obtain aerostatic air bearing, each rotor 52 is provided with air bearing jets. Owing to the electromagnetic dynamic effect between the rotor 52 and stator 51, the air bearing is under great bias so that at operating pressure the air gap is very constant. The service life is advantageously in principle unlimited since friction and wear and tear do not occur. Lubricants are also unnecessary. This facilitates the preferred use in the field of medicine.

For an embodiment of the ion beam scanning system according to the invention, the linear motor was so designed that two motors move on the same stator in opposite directions in the direction of arrow A, as shown in FIG. 1. For that purpose, the dimensions of the stator are 64 mm×64 mm×1 m in length, of which only about 50 cm length are required for the depth scanner. The stator also has a lamellar structure having a period of 1.28 mm. The motors are mounted on air bearings and in principle operate in the manner of magnetic levitation. The technical data of the motors is as follows:

| | |
|---|---|
| Mass: | 700 g |
| Maximum holding force: | 100 N |
| Maximum speed: | 2 m/s |
| Maximum acceleration; | 40 m/s$^2$ |
| Positional accuracy: | 10 μm |
| Repeat accuracy: | 3 μm |
| Guiding accuracy: | 5 μm |
| Air pressure bearing; | 3.5 bar |

Advantageously, the stepper motor control 35, as shown in FIG. 1, position 35, is suitable for a depth scanner or a depth modulator. The stepper motor control 35 has a simple effective interface that consists substantially of only 2 TL inputs 80, 81, which give a step command or a direction command. In the case of a step command, the motor currents of the power stage are so altered with each incoming TTL pulse at a first input 80 that the motors continue to move in opposite directions by 20 μm in that example. For a direction command, the level (TTL) at the second input 81 determines the direction, that is to say movement apart or movement towards one another.

The ionisation chamber 16, as shown in FIG. 1, indicates the number of particles (heavy ions) extracted per second by the accelerator. That value is subject to large temporal variations and must therefore be measured in real time. For that purpose, there is used a parallel-plate transmission ionisation chamber having a gas distance of about 1 cm (nitrogen-$CO_2$ mixture: 80/20%), which is operated at 1600 V. The current that can be measured at the outlet of the chamber is proportional to the beam current when the particle energy remains the same. At typical beam currents of the accelerator, the currents from the ionisation chamber are in the region of μA.

The response speed of the detector is limited by the drift time of the ionised detector molecules (ion cores) in the ionisation chamber 16 and has a delay constant of about 100 μs.

The measuring electronics in the current amplifier block 33 convert the current from the ionisation chamber to a proportional frequency of TTL pulses. A voltage signal in the Volt range is produced from the current signal. TTL pulses are produced from the voltage signal by amplitude-frequency conversion, the frequency of which pulses is proportional to the voltage. 4 MHz correspond to about 10 V.

At a given amplification of the current amplifier 33 of FIG. 1, a TTL pulse accordingly corresponds to a specific charge produced in the ionisation chamber, which was in turn produced by a specific particle count. The number of TTL pulses produced is thus proportional to the number of heavy ions flying through the ionisation chamber 16. The proportionality factor can be determined experimentally to an accuracy of ±3% and is dependent upon the particle energy and amplification.

The pulse control 34 in FIG. 1 is, in principle, a variable pulse rate converter. The control system has a memory that can be divided into a plurality of regions. By way of the connected PC, a series of figures can be entered for each of the individual regions before irradiation. The number of figures corresponds to the number of positions that the linear motors are to adopt for a depth scan, which, in practice, will be several thousand positions per region.

When the irradiation is started, the pulse control counts the pulses coming from the measuring electronics and for its part sends a pulse to the stepper motor control 35 when the pulse count for the first position has been reached. The counter is then reset to 0 and counting is carried out again until the pulse count for the second position has been reached, whereupon a TTL pulse is emitted again. That procedure is repeated until the final position has been reached. The pulse control then sends a stop signal to the accelerator, whereupon the beam extraction is terminated within a few μs.

Directly thereafter the next memory region having a different series of figures can be activated in order to carry out a different depth scan. The computer 60 and monitor 14 for control means is used to load the series of figures into the pulse control. Moreover, the computer can control the stepper motor control 35 directly by way of an index card. The motors can thus be moved automatically to their reference position or start position before the actual depth scan.

Figure 10:
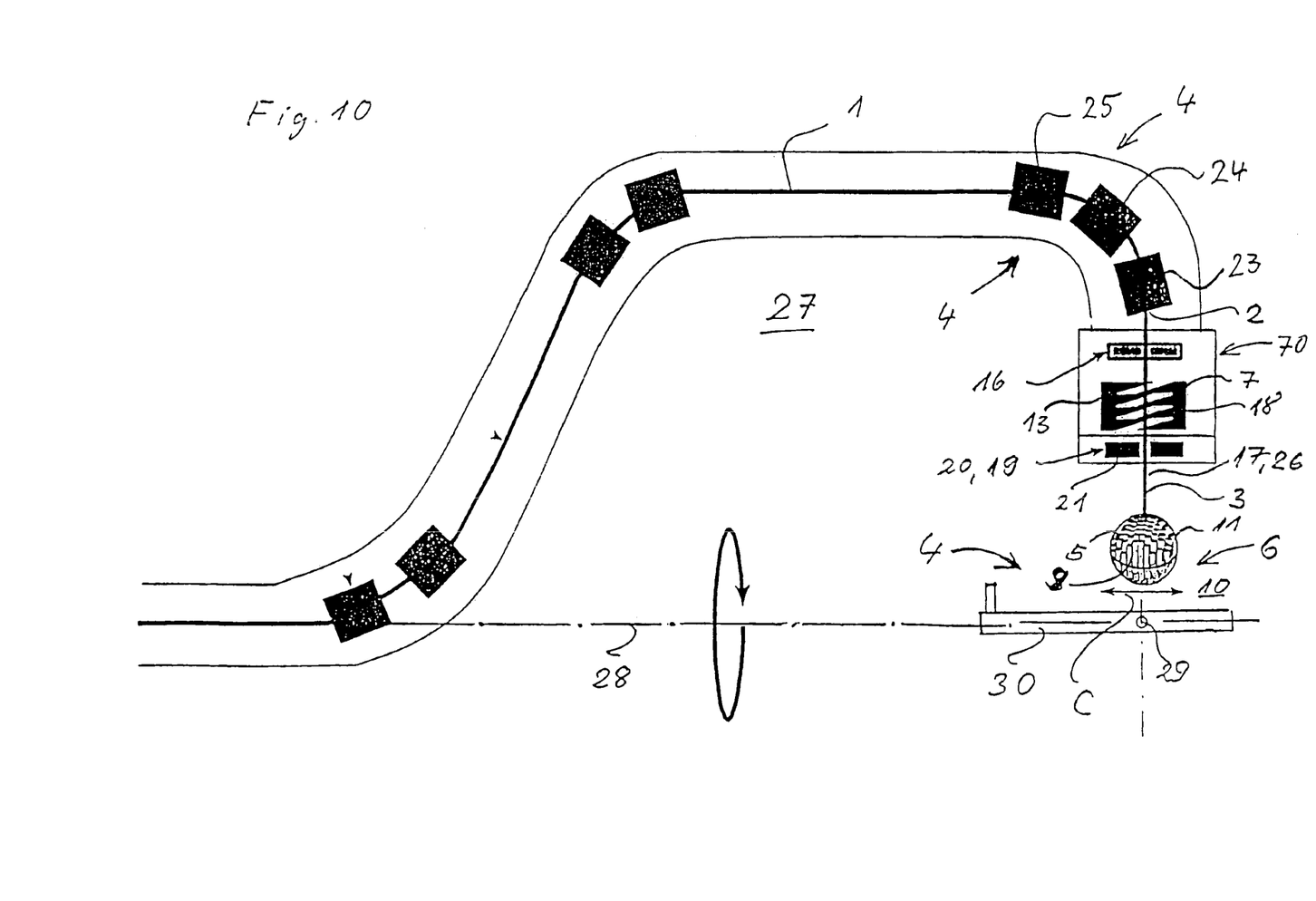
FIG. 10 is a schematic diagram of a second embodiment of the invention.

FIG. 10 shows a second embodiment of the invention. The depth scanner 70 corresponds to the depth of FIG. 1 in the manner of its construction and its operation.

However, in this preferred application, a gantry system is used, which enables the ion beam 3 in a controlled ion beam 26 to be rotated about a gantry axis of rotation 28. By means of the depth modulator or depth scanner 70, the target volume 5 can be scanned in columns and by rotating the gantry system by a few degrees of angle, the target volume can be scanned literally. A particular advantage of that arrangement is the possibility of arranging the target volume above the isocentre 29 of the gantry system 27. The inlet channel for the ion beam is thus divergent in the upstream direction, which means that both the skin of a patient and also healthy tissue are subjected to less irradiation because the ion beam irradiation in the region above the target volume 5 is distributed over a greater volume. By using the gantry system according to FIG. 10, the target volume carrier 30 has to be moved in one direction only, preferably in the direction of the gantry axis of rotation 28, as shown by the arrow directions C.

Figure 11:
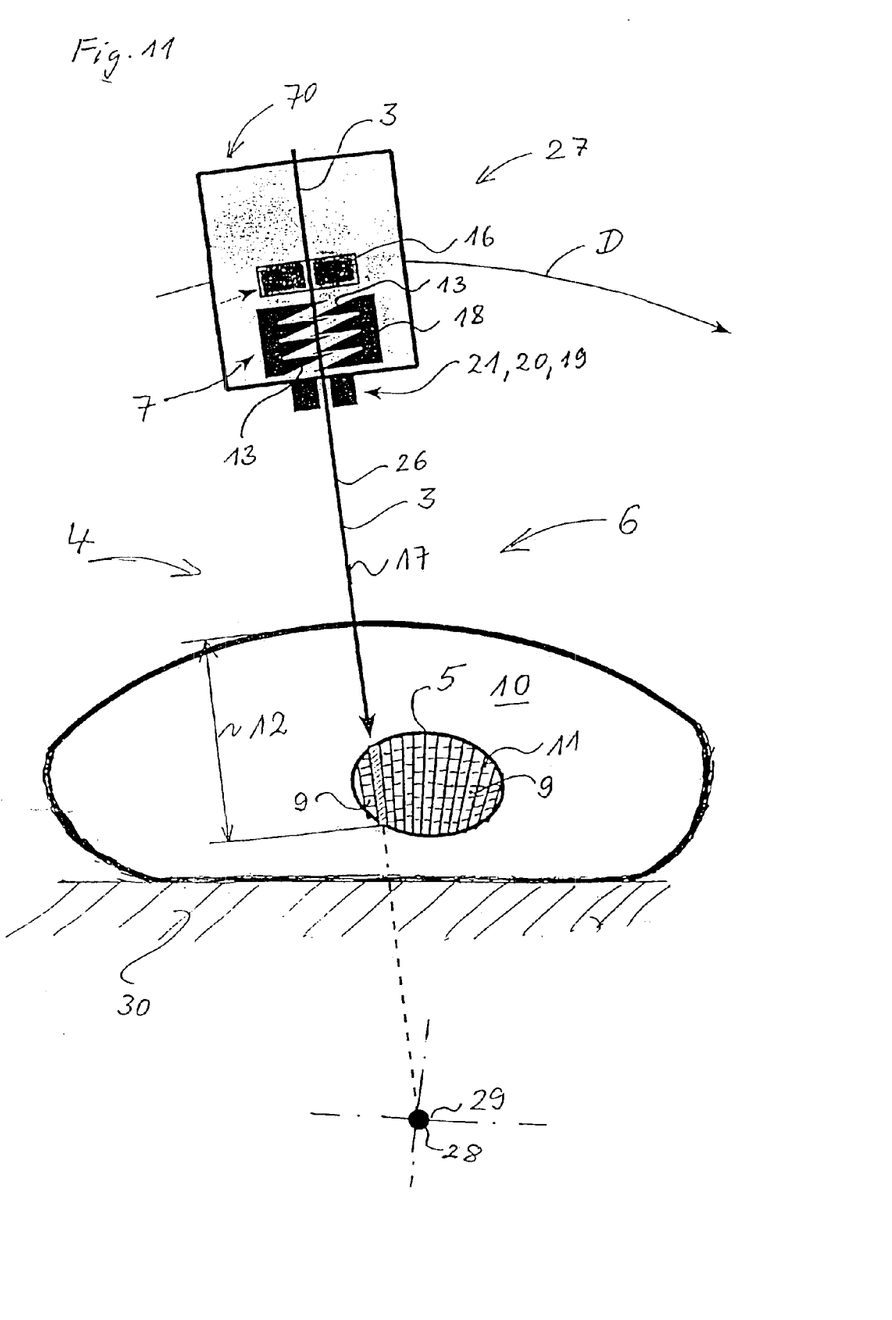
FIG. 11 is a schematic diagram of the arrangement above the isocentre of a target volume in the embodiment according to FIG. 10.

FIG. 11 is a schematic diagram of the arrangement of a target volume 5 in the embodiment according to FIG. 10 above the isocentre 29. That schematic diagram shows clearly the direction of gantry rotation D in which the target volume 5 is depth-scanned in successive columns using the depth scanner 70. For each volume element 9, the number of ions is measured in the ionisation chamber 16 and, if necessary, a sharp edge cut-off can be adjusted near the edges of the tumour tissue by means of the edge-delimitation device 20. It can also be seen clearly that the irradiation of healthy tissue 10 above the tumour tissue is distributed over a relatively large volume so that the amount of radiation to which healthy tissue is subjected is reduced.

Figure 12:
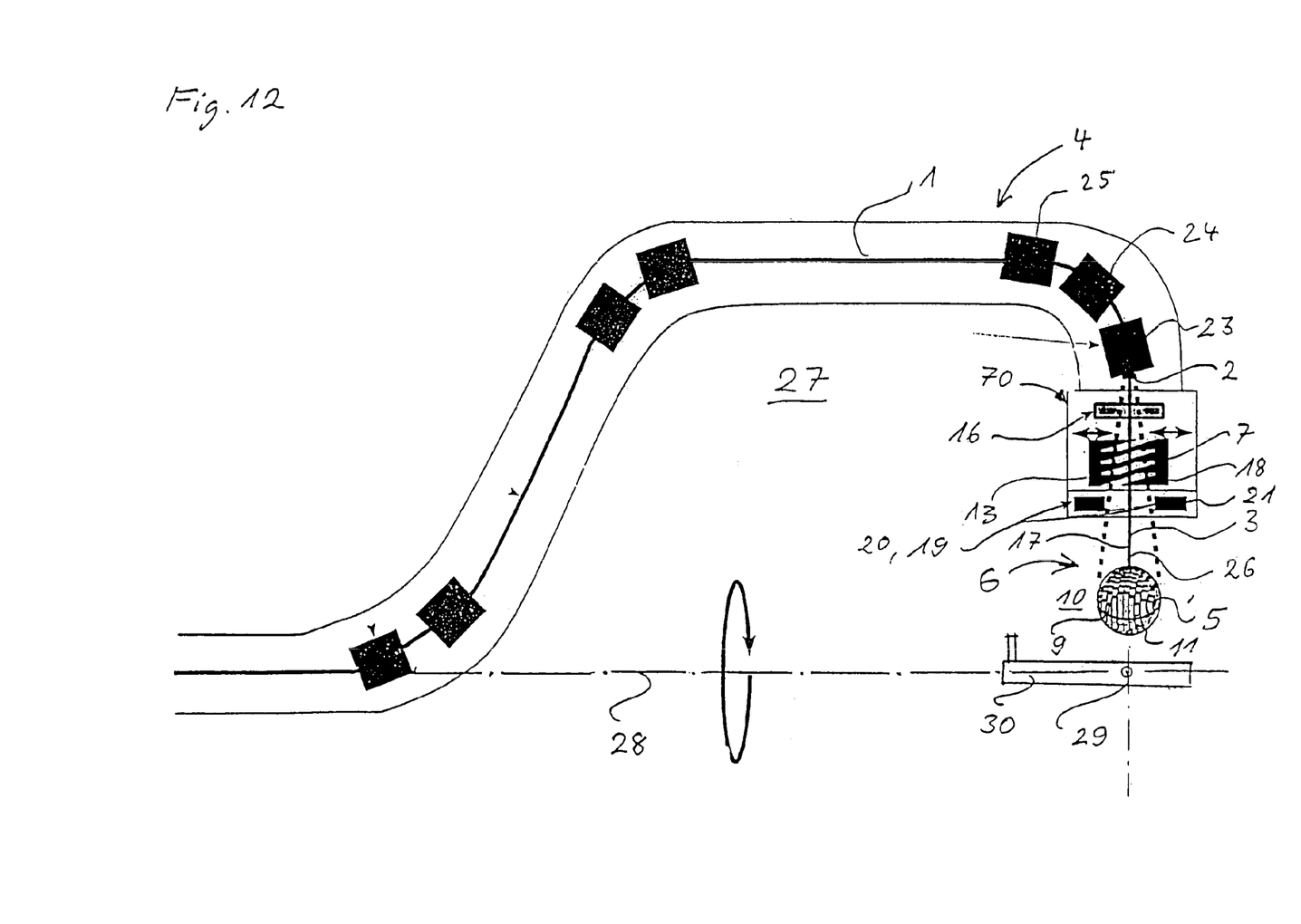
FIG. 12 is a schematic diagram of a third embodiment of the invention.

Whereas in the system shown in FIGS. 10 and 11 the target volume carrier 30 has to be moved in the longitudinal direction in order to irradiate all of the target volume, FIG. 12 is a schematic diagram of a third embodiment of the invention in which no further mechanical movement of the target volume is necessary after alignment of the target volume relative to the isocentre. In the embodiment according to FIG. 12 showing gantry 4, instead of the target volume carrier, it is the ion beam that is deflected in the beam guidance plane of the gantry system by means of the deflection magnets 23, 24 and 25 of the ion beam guidance system in the gantry system, which does not require much greater outlay for the currents in the deflection magnets since it is not necessary to redesign the deflection magnets because the ion beam would be deflected in the direction of the dipole gap of the last deflection magnets. In that system the same depth scanner 70 is used as in the first and second embodiments of the invention according to FIG. 1 and FIG. 10.

What is claimed is:

1. An ion beam scanning system having an ion source device, an ion accelerator system that can be set to an acceleration of ions required to obtain a maximum depth of penetration, and an ion beam guidance system (1) comprising an ion beam outlet window (2) for a converging centred ion beam (3), and a mechanical alignment system (4) for a target volume (5) to be scanned, wherein the scanning system (6) comprises energy absorption means (7) that are arranged in the path of the ion beam between the target volume (5) and the ion beam outlet window (2) transverse to the centre of the ion beam and comprises absorber wedges (13) that can be displaced transverse to the centre of the ion beam, a high-performance linear motor (8) for rapid driving of the absorber wedges (13) and beam-intensity-controlled depth-scanning with transverse displacement of the energy absorption means (7), so that depth-staggered scanning of volume elements (9) of a tumour tissue (11) can be carried out in rapid succession, and an ionisation chamber (16) for measuring beam intensity, which is arranged upstream of the energy absorption means (7).

2. The ion beam scanning system according to claim 1, wherein the target volume (5) is the tumour tissue (11) surrounded by healthy tissue (10), and wherein the depth of penetration (12) of the ion beam (3) is determined by energy of the ions in the ion beam (3) and a deepest region of the tumour tissue (11) can be reached by means of the variable acceleration of the ions.

3. The ion beam scanning system according to claim 1, wherein the scanning system further comprises an electronic control system (14, 34) for the linear drive of the absorber wedges (13) and includes an ionisation chamber (16) for measuring the particle rate of the beam and moves the absorber wedges (13) closer together by a step, when a predetermined particle count has been reached, which particle count may be different for each depth step, so enabling depth-staggered scanning of volume elements (9) of the target volume (5).

4. The ion scanning system according to claim 3, wherein the step is from 10 μm to 100 μm.

5. The ion beam scanning system according to claim 1, wherein the energy absorption means (7) comprise at least two absorber wedges (13) that can be displaced in opposite directions transverse to the centre of the ion beam.

6. The ion beam scanning system according to claim 1, wherein the energy absorption means (7) comprise two absorber wedge assemblies (18) that can be opposite transverse to the centre (17) of the ion beam.

7. The ion scanning system according to claim 1, wherein the scanning system further comprises an edge-delimitation device (20) having displaceable shutter elements (21) between the target volume (5) and the energy absorption means (7).

8. The ion beam scanning according to claim 1, wherein the scanning system further comprises edge shutters (19) that can be adjusted separately in the manner of an iris diaphragm in order to delimit some of an edge of the ion beam (3) with respect to the target volume.

9. The ion beam scanning system according to claim 1, further comprising a patient table (22) that carries the target volume (5) and that can be displaced in a plane transverse to the ion beam (3) in two directions of co-ordinates during an irradiation procedure.

10. The ion beam scanning system according to claim 1, further comprising a patient table (22) that carries the target volume (5) and that can be displaced in a lateral direction transverse to the ion beam (3) during an irradiation procedure and has deflection magnets (23, 24, 25) that deflect the ion beam (3) from its central position at the outlet window (2) transverse to the lateral direction of the patient table (22).

11. The ion beam scanning system according to claim 1, wherein the intensity of the ion beam scanning is defined by a total number of ions that strike the volume element (9).

12. The ion beam scanning system according to claim 1, further comprising a patient table (22) that carries the target volume (5) and that can be displaced in a lateral direction transverse to the ion beam (3) during irradiation, and a gantry system (27) that can be rotated about a gantry area axis of rotation transverse to the lateral direction of movement of the patient table (22).

13. The ion beam scanning system having the gantry system (27) for aligning the ion beam (3) with the target volume (5) according to claim 12, wherein the ion beam (3) is supplied to the gantry system (27) in the gantry axis of rotation (28) and can be aligned with a target volume (5) by means of magneto-optics (23, 24, 25) at adjustable angles of from 0 to 360° in a plane orthogonal to the gantry axis of rotation (28) so that the ion bean (3) intersects the gantry axis of rotation (28) at an isocentre (29) of the gantry system (27), wherein the gantry system (27) comprises a target volume carrier (30) that can be displaced laterally in the direction of the gantry axis of rotation (28), the target volume (5) is arranged upstream of the isocentre (29) and energy absorption means (7), which are arranged radially upstream of the gantry system (27), define volume element scanning in a depth direction, the gantry system (27) defines angular volume element scanning in a lateral direction and the laterally displaceable target volume carrier (30) defines volume element scanning in a longitudinal direction, and target volumes (5) of any shape can be scanned by volume element by a combination of the energy absorption means (7), the gantry system (27) and the target volume carrier (30).

14. The ion beam scanning system having the gantry system according to claim 13 wherein the target volume carrier (30) remains stationary during irradiation and the deflection magnets (23, 24, 25) deflect the ion beam (3) in the gantry plane during irradiation.

15. The ion beam scanning system having the gantry system according to claim 13, wherein the energy absorption means (7) comprise absorber wedges (13) that can be displaced tangential to a circle rotation of the gantry system (27).

16. The ion beam scanning system having the gantry system according to claim 13, wherein the energy absorption means (7) comprise at least two absorber wedges (13) that can be displaced in opposite directions tangential to a circle of rotation of the gantry system (27).

17. The ion beam scanning system having the gantry system according to claim 13, wherein the energy absorption means (7) comprise absorber wedge assembles (18) that can be displaced in a radially staggered manner tangential to a circle of rotation of the gantry system (27).

18. An ion beam scanning system having an ion source device, an ion accelerator system that can be set to an acceleration of ions required to obtain a maximum depth of penetration, and an ion beam guidance system (3), and a mechanical alignment system (4) for a target volume (5) to be scanned, wherein the scanning system (6) comprises energy absorption means (7) that are arranged in the path of the ion beam between the target volume (5) and the ion beam outlet window (2) transverse to the centre of the ion beam and comprises absorber wedges (13) that can be displaced transverse to the centre of the ion beam, a high-performance linear motor (8) for rapid driving of the absorber wedges (13) and beam-intensity-controlled depth-scanning with transverse displacement of the energy absorption means (7), so that the depth-staggering scanning of volume elements (9) of a tumour tissue (11) can be carried out in rapid succession, and a patient table (22) that carries the target volume (5) and that can be displaced in a lateral direction transverse to the ion beam (3) during irradiation, and a gantry system (27) that can be rotated about a gantry area axis of rotation transverse to the lateral direction of movement of the patient table (22) and wherein the ion beam (3) is supplied to the gantry system (27) in the gantry axis of rotation (28) and can be aligned with a target volume (5) by means of magneto-optics (23, 24, 25) at adjustable angles of from 0 to 360° in a plane orthogonal to the gantry axis of rotation (28) so that the ion bean (3) intersects the gantry axis of rotation (28) at an isocentre (29) of the gantry system (27), wherein the gantry system (27) comprises a target volume carrier (30) that can be displaced laterally in the direction of the gantry axis of rotation (28), the target volume (5) is arranged upstream of the isocentre (29) and energy absorption means (7), which are arranged radially upstream of the gantry system (27), define volume element scanning in a depth direction, the gantry system (27) defines angular volume element scanning in a lateral direction and the laterally displaceable target volume carrier (30) defines volume elements scanning in a longitudinal direction, and target volumes (5) of any shape can be scanned by volume element by a combination of the energy absorption means (7), the gantry system (27) and the target volume carrier (30) and wherein a central region of the target volume (5) is arranged upstream of the isocentre (29) by at least one fifth of a radius of the gantry system, so that the target volume (5) does not lie in the isocentre (29).

19. A method of ion beam scanning using an ion source device, an ion accelerator system and an ion beam guidance system (1) comprising an ion beam outlet window (2) for a converging centered ion beam (3), and a mechanical alignment system (4) for scanning a target volume (5), the scanning system (6) comprising energy absorption means (7) and an ionisation chamber (16), which is arranged upstream of the energy absorption means (7), comprising the steps of:

setting the ion accelerator system to an acceleration of the ions required to obtain a maximum depth of penetration (12), detecting ion beam intensity, traversing displacement of the energy absorption means (7) of variable thickness for depth modulation of the ion bean (3), summing radiation ions of a volume element (9) of the target volume (5) up to a predetermined radiation dose, altering the depth of penetration of the ion beam (3) by means of transverse displacement of the energy absorption means (7) when the predetermined radiation dose of the volume element (9) has been reached in order to irradiate a next upstream volume element.

20. The method of operating an ion beam scanning system according to claim 19 using a gantry system (27), wherein a target volume carrier (30) is aligned before irradiation and remains stationary during irradiation and the ion beam (3) is deflected in the gantry plane by means of the last gantry deflecting magnets (23, 24, 25) in order to carry out volume element scanning in a longitudinal direction.

21. The method according to claim 19, wherein an electronic control system (14) for a linear drive of the absorber wedges (13) measures a particle rate of the beam by means of the ionisation chamber (16) and moves the absorber wedges (13) closer together by a step, after a predetermined particle rate has been reached, which particle rate may be different for each depth step, so that a depth-staggered scanning of volume elements (9) of the target volume (5) is effected.

22. The method according to claim 21, wherein the step is from 10 $\mu$m to 100 $\mu$m.

23. A method of ion beam scanning using an ion source device, an ion accelerator system and an ion beam guidance system (1) comprising an ion beam outlet window (2) for a converging centered ion beam (3), and a mechanical alignment system (4) for scanning a target volume (5), the scanning system (6) comprising energy absorption means (7) and an ionisation chamber (16), which is arranged upstream of the energy absorption means (7), comprising the steps of:

setting the ion accelerator system to an acceleration of the ions required to obtain a maximum depth of penetration (12), detecting ion beam intensity, traversing displacement of the energy absorption means (7) of variable thickness for depth modulation of the ion beam (3), summing radiation ions of a volume element (9) of the target volume (5) up to a predetermined radiation dose, altering the depth of penetration of the ion beam (3) by means of transverse displacement of the energy absorption means (7) when the predetermined radiation doses of the volume element (9) has been reached in order to irradiate the next upstream volume element wherein the intensity is adjusted to from $10^6$ to $10^8$ absorbed ions per volume unit during scanning of the target volume (5).

24. The method according to claim 19, wherein the scanning of the volume of the target volume (5) progresses continuously.

25. The method according to claim 19, wherein the scanning of the volume of the target volume (5) in a depth direction is effected by columns.

26. The method according to claim 19, wherein the scanning of the volume of the target volume (5) proceeds stepwise.

27. The method according to claim 19, wherein the scanning of the target volume (5) is carried out continuously in a depth direction and stepwise in a lateral and longitudinal directions.

28. The method according to claim 19, wherein the scanning of the volume of the target volume (5) is carried out continuously in a depth direction and in a lateral direction and stepwise in a longitudinal direction.

29. The method of operating in ion beam scanning system according to claim 19 using a gantry system (27) for aligning the ion beam (3) with the target volume (5), wherein the ion beam (3) is supplied to the gantry system (27) in an axis of rotation and is aligned with the target volume (5) by means of magneto-optics (23, 24, 25) at adjustable angles of from 0 to 360° in a plane orthogonal to the gantry axis of rotation (28), so that the ion beam (3) intersects the gantry axis of rotation (28) at an isocentre (29) of the gantry displaced laterally in the direction of the gantry axis of rotation (28), comprising the steps of: arranging the target volume (5) upstream of an isocentre (29), scanning the volume element in a depth direction by means of energy absorption means (7) arranged radially upstream of the gantry system (27), scanning the volume element in a lateral direction by altering the angle of rotation of the gantry system (27), and scanning of the volume element in a longitudinal direction by lateral displacement of the target volume carrier (30).

30. An ion beam scanning system having an ion source device, an ion accelerator system that can be set to an acceleration of ions required to obtain a maximum depth of penetration, and an ion beam guidance system (1) comprising an ion beam outlet window (2) for a converging centred ion beam (3), and a mechanical alignment system (4) for a target volume (5) to be scanned, wherein the scanning system (6) comprises energy absorption means (7) that are arranged in the path of the ion beam between the target volume (5) and the ion beam outlet window (2) transverse to the centre of the ion beam and comprises absorber wedges (13) that can be displaced transverse to the centre of the ion beam, a high-performance linear motor (8) for rapid driving of the absorber wedges (13) and beam-intensity-controlled depth-scanning with transverse displacement of the energy absorption means (7), so that depth-staggered scanning of volume elements (9) of a tumour tissue (11) can be carried out in rapid succession and wherein the linear motor comprises rotors (31) mounted on air bearings.

* * * * *